United States Patent
Zimmerle et al.

(10) Patent No.: US 9,658,152 B2
(45) Date of Patent: May 23, 2017

(54) OPTICAL INTERPRETATION OF ASSAY RESULTS

(71) Applicant: Siemens Healthcare Diagnostics Inc., Tarrytown, NY (US)

(72) Inventors: Chris Thomas Zimmerle, Goshen, IN (US); Gary W. Rheinheimer, Goshen, IN (US); James Arthur Profitt, Palmer Lake, CO (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/817,654

(22) Filed: Aug. 4, 2015

(65) Prior Publication Data
US 2016/0041152 A1   Feb. 11, 2016

Related U.S. Application Data

(60) Provisional application No. 62/033,332, filed on Aug. 5, 2014.

(51) Int. Cl.
*G01N 21/25* (2006.01)
*G02B 27/28* (2006.01)
*G01N 21/84* (2006.01)

(52) U.S. Cl.
CPC ......... *G01N 21/251* (2013.01); *G02B 27/286* (2013.01); *G01N 21/8483* (2013.01)

(58) Field of Classification Search
CPC ... G01N 33/53; G01N 21/251; G01N 21/8483
USPC ......................................................... 356/408
See application file for complete search history.

(56) References Cited

U.S. PATENT DOCUMENTS

| 8,145,431 | B2 | 3/2012 | Kloepfer et al. |
| 8,947,656 | B2 | 2/2015 | Cunningham |
| 9,241,663 | B2 | 1/2016 | Jena et al. |
| 2014/0120563 | A1* | 5/2014 | Ozcan ................ G01N 21/78 435/7.94 |
| 2015/0055134 | A1* | 2/2015 | Papautsky ............ G01N 21/25 356/408 |
| 2015/0359458 | A1* | 12/2015 | Erickson ............... G01N 33/52 455/557 |

FOREIGN PATENT DOCUMENTS

WO   2014113770 A1   7/2014

* cited by examiner

*Primary Examiner* — Kara E Geisel
*Assistant Examiner* — Hina F Ayub
(74) *Attorney, Agent, or Firm* — Kyle D. Petaja

(57) ABSTRACT

The inventive concepts disclosed herein are generally directed to the use of a hand-held mobile computing device, such a smartphone or tablet, to interpret the results of a medical assay device. By controlling conditions like image placement and illumination and correcting for imperfect illumination, accurate results can be obtained with hand-held mobile computing device.

13 Claims, 8 Drawing Sheets

OPTICAL INTERPRETATION OF ASSAY RESULTS

The subject application claims benefit under 35 USC §119(e) of U.S. provisional Application No. 62/033,332, filed Aug. 5, 2014. The entire contents of the above-referenced patent application are hereby expressly incorporated herein by reference.

BACKGROUND

1. Field of the Disclosure

This disclosure relates to the use of mobile computing devices to interpret the results of assay devices.

2. Brief Description of the Related Art

The analysis of assay devices such as, but not limited to, analyte assay devices (e.g., urine dip-strip) and immunoassay flow devices have commonly be done in laboratories by trained personnel on dedicated instruments. Recently, however, crude smartphone software applications have been introduced that utilize the smartphone's onboard camera. However, further development is needed in order to improve accuracy.

SUMMARY OF THE INVENTIVE CONCEPT(S)

In one aspect, the inventive concepts disclosed herein are directed to a stand for a mobile computing device. The stand having a reading location, a raised platform, a light source, a first polarized lens, a second polarized lens, and at least one exterior surface. The reading location being capable of supporting an assay device having a testing region. The raised platform disposed a distance above the reading location along a line extending from the raised platform to the reading location. The raised platform having a through hole, the through hole capable of being aligned with a camera on the mobile computing device when the mobile computing device is placed on the raised platform. A light source disposed between the reading location and the raised platform, the light source directing light at the assay reading location area substantially along the line, the light source allowing the camera an unobstructed view the testing area of the assay device when the camera of the mobile computing device is aligned with the through hole and when an assay device is placed on the reading location. The first polarized lens is disposed between the light source and the assay reading location, wherein substantially all of the light emanating from the light source passes through the first polarized lens, wherein the first polarized lens is polarized in a first direction. The second polarized lens disposed between the camera and the assay reading location, wherein when the camera of the mobile computing device is aligned with the through hole and when an assay device is placed on the reading location, the testing region of the assay device is visible to the camera through the second polarized lens, wherein the second polarized lens is polarized in a second direction that is perpendicular to the first direction. The combination of the raised platform and the at least one exterior surface reduces the amount of external light reaching the reading location, wherein external light is lighting emanating from outside of the stand.

In another aspect of the invention, the stand may include at least one reference device located adjacent to the reading location on a first side of the assay device when the assay device is supported by the reading location. The reference device containing a reference testing region, the reference testing region having known reference color values, the reference testing region being aligned with the testing region of the assay device when the assay device is being supported by the reading location.

In yet another aspect of the invention, a computer-readable storage medium on which computer-executable instructions are stored is described. The computer-executable instructions, when executed by a computing device, implement a method of using the stand. The method implemented by the computer-executable instructions comprising the following. Receiving the known reference color values of the reference testing region. Obtaining at least one measured color value of the testing region of the assay device and a corresponding measured color value of the reference testing region of the reference device. Receiving and comparing the known reference color values of the reference testing region to the measured color value of the testing region. Using the known reference color values to correct the measured color values and producing a corrected color value. Using the corrected color value to determine a result of the assay.

In an aspect of the invention, a computer-readable storage medium on which computer-executable instructions are stored is described. The computer-executable instructions, when executed by a computing device, implement a method of interpreting the test region of an assay device. The method implemented by the computer-executable instructions comprising the following. Receiving a plurality of RGB values obtained by a camera operatively coupled to the processor, the plurality of RGB values corresponding to a testing region of the assay device, the testing region having a plurality of different testing pads arranged in a known order. Identifying a location of an anchor testing pad in the testing region matching a predefined RGB signature. Determining the position of a second testing pad based on the location of the anchor testing pad.

BRIEF DESCRIPTIONS OF THE DRAWINGS

FIGS. 4A, 4B, 4C, 5A, and 5B illustrate a correction algorithm.

Figure 6:
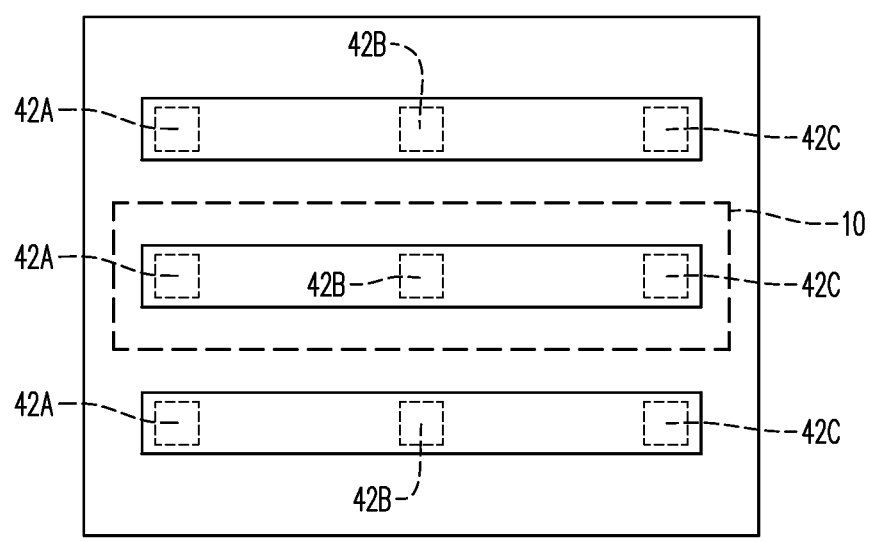

FIG. 6 illustrates an example photograph taken by the camera of the mobile computing device.

Figure 7:
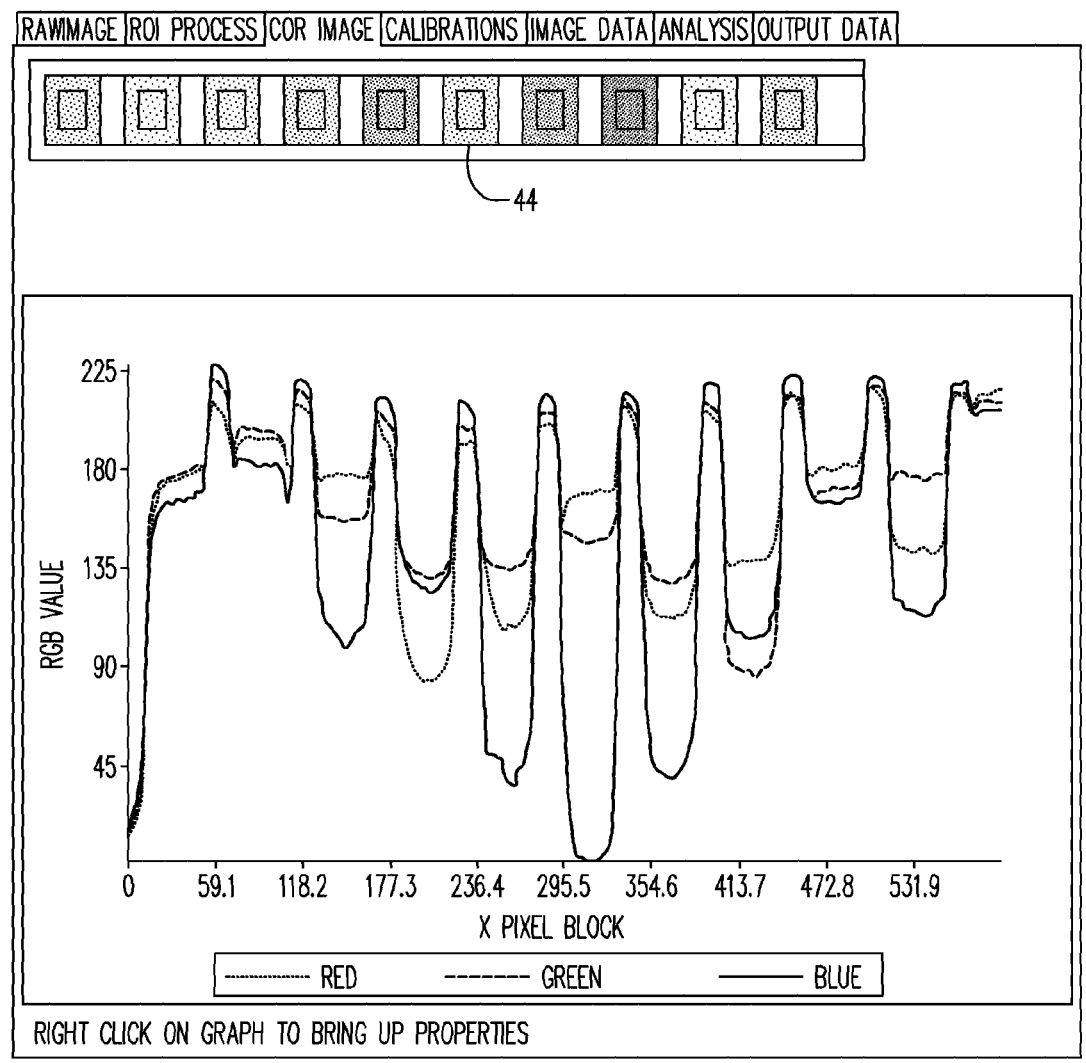

FIG. 7 depicts an illustrative assay device.

Figure 8:
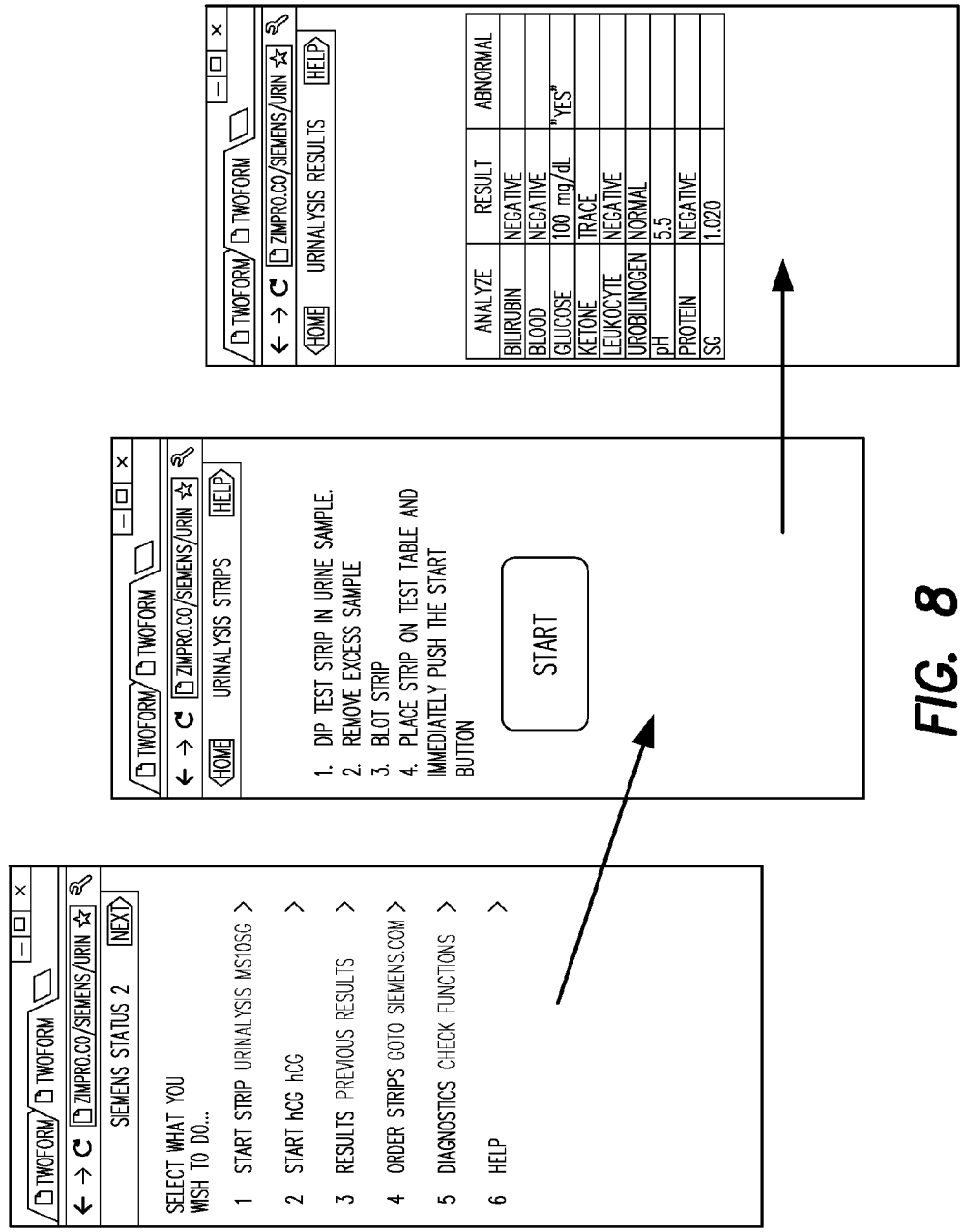

FIG. 8 depicts an illustrative user interface.

DETAILED DESCRIPTION OF THE INVENTIVE CONCEPT(S)

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The inventive concepts disclosed herein are generally directed to the use of a hand-held mobile computing device, such a smartphone or tablet, to interpret the results of a medical assay device. By controlling conditions like image placement and illumination and correcting for imperfect illumination, accurate results can be obtained with hand-held mobile computing device. When all or part of a medical assay device is illuminated, a reflectance signal may be used in evaluating the assay device and making a determination of the presence and/or level of one or more analytes in a sample. It is important that the illumination is either entirely uniform in the area observed, which is difficult and expensive, or that the illumination be corrected across all of the small regions comprising the whole area of interest (e.g., the testing area of the medical assay device).

Another aspect of the invention includes a stand which reduces or substantially excludes external light, secures/supports the imaging device during image capture, illuminates the assay device with polarized light, positions the camera to maximize the pixel coverage of the testing region of the assay, reduces specular reflectance, supports one or more reference materials (which helps correct for differences in camera and light illumination), and positions the camera at an optimal focal length from the assay device.

One aspect of this invention provides a device and a method which compensates for illumination which is less than perfect. For example, an embodiment of the stand may include one or more reference devices located within the stand and close to the assay device. These reference devices may be used by the mobile computing device to compensate for less than ideal lighting. It should also be appreciated that similar reference devices can be incorporated into various other diagnostic instruments (including traditional diagnostic devices) and are not limited to the stand 2 described below. Similarly, the methods described below can be adapted for use in a variety of other diagnostic instruments.

In yet another aspect of the invention, a technique is described for locating a specific testing pad in the testing region of the of the assay device and using the location of the specific testing pad in order to locate other testing pads in the testing region.

It should be appreciated that while the various aspect of this invention are described with respect to Red, Green, Blue (RGB) sensors, a person of ordinary skill should appreciate that the invention is not so limited. It should also be noted that illuminators based upon inexpensive white LED components may produce illumination patterns which differ in intensity distribution when sensed by Red, Green, or Blue-sensitive sensors. The invention demonstrates independent application to the three common sensor channels (RGB for Red, Green, and Blue).

Figure 1:
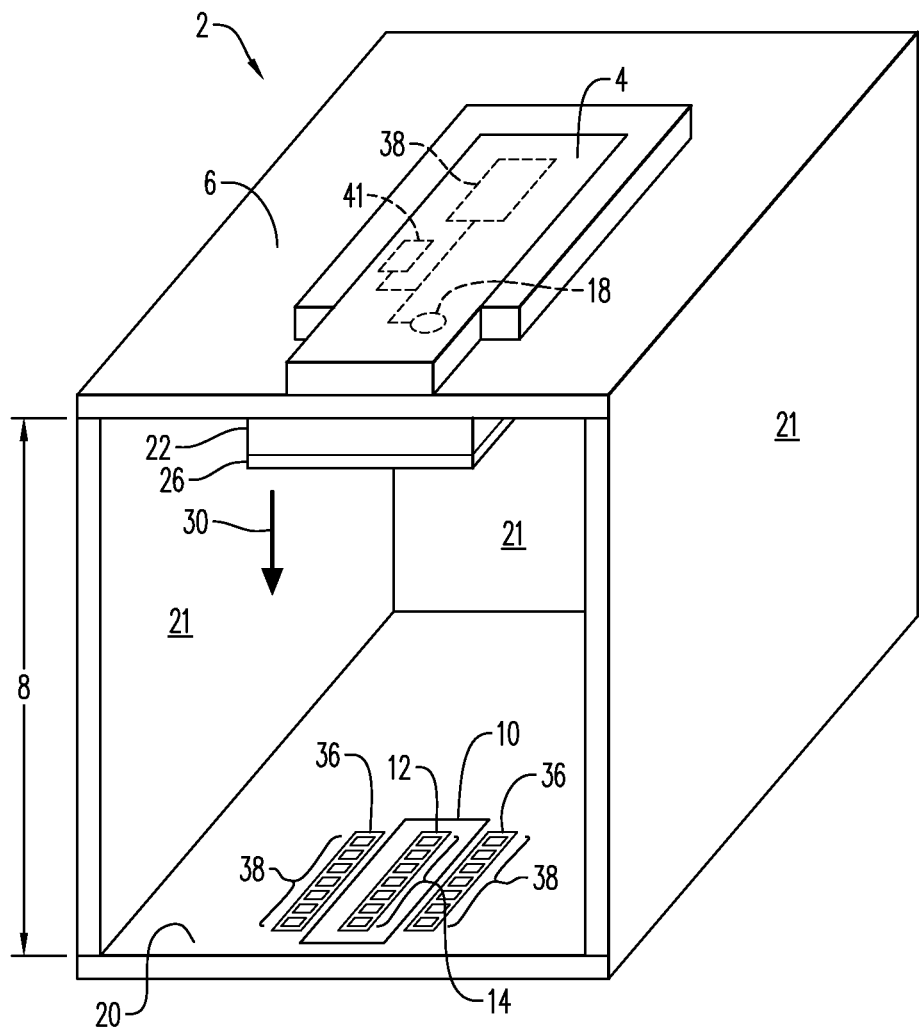
FIG. 1 illustrates a perspective view of an embodiment of a stand for a mobile computing device with a front surface removed for clarity.
Figure 2:
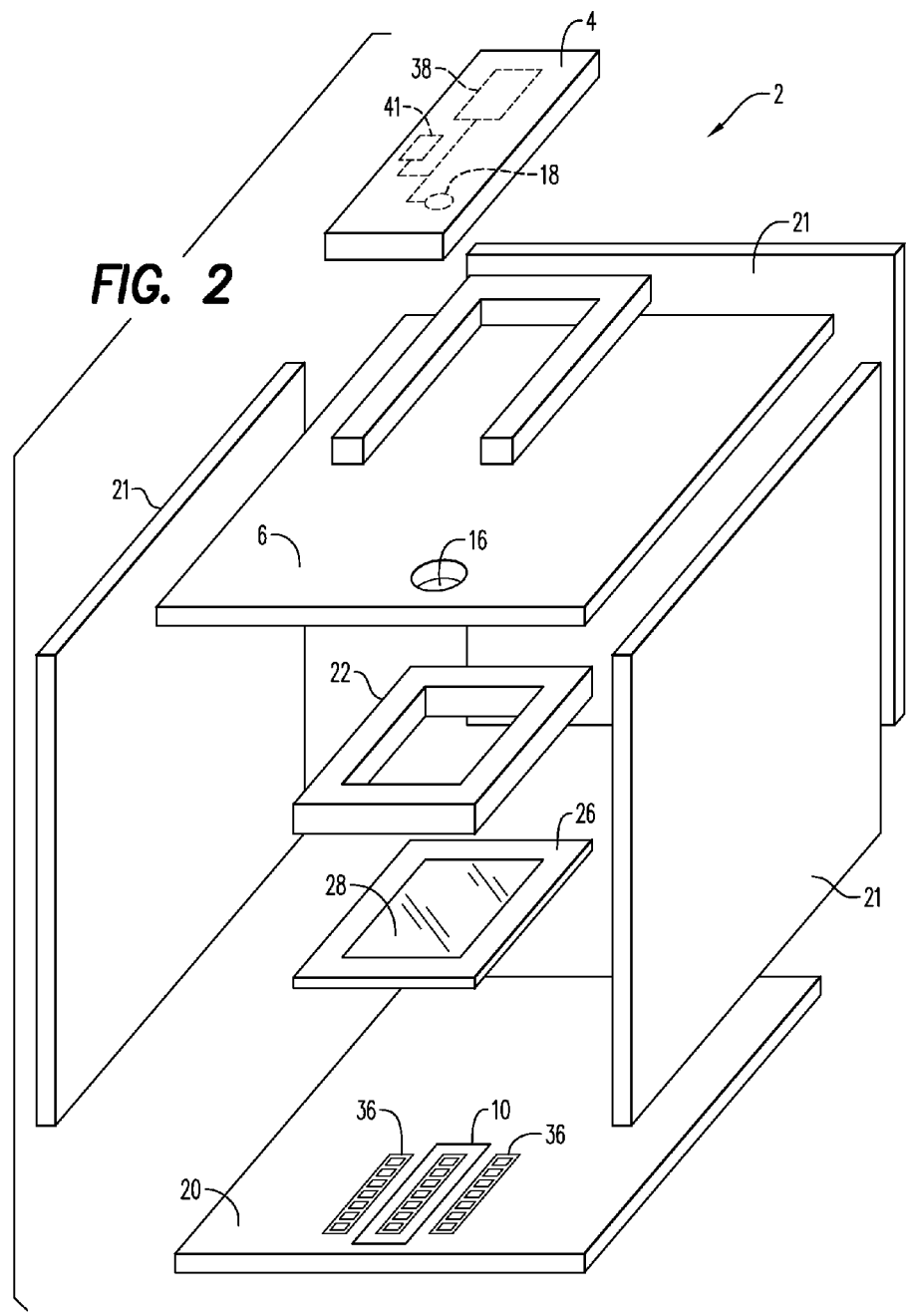
FIG. 2 illustrates an exploded view of the stand in FIG. 1.

FIGS. 1 and 2 illustrate a stand 2 which is capable of supporting a mobile computing device 4 on a raised platform 6 disposed at a distance 8 above a reading location 10 on lower surface 20. The reading location 10 is capable of supporting an assay device 12, the assay device 12 containing a testing region 14. Stand 2 additionally contains one or more exterior surfaces 21 which can combine to restrict the amount of external light emanating from outside of the stand from reaching the reading location 10. Alternatively, the stand 2 may prevent substantially all external light from reaching the reading location 10. For example, the embodiment of stand 2 in FIGS. 1 and 2 take the form of a box capable of preventing most external light from reaching the reading location 10 (note that front wall of the stand 2 in FIGS. 1 and 2 is not shown for clarity). It should be understood that the assay device 12 may be inserted/removed from the stand 2 in a variety of ways (for example, but not limited to, a removable door or a port in the raised platform 6 or an external surface 20).

The raised platform 6 of stand 2 has a through hole 16, extending completely there through. When the mobile computing device 4 is placed on the raised platform 6, a camera 18 on the mobile computing device 4 can be aligned with the through hole 16. This configuration allows the camera 18 to view the assay device 12, or at least the entirety of the testing region 14 of the assay device 12. A person of ordinary skill in the art should also appreciate that the mobile computing device 4 contains a processor 40 coupled to the camera 18.

Reading location 10 generally refers to the area within which the assay device 12 should be placed in order to be visible through the through hole 16. Reading location 10 can be denoted by markings and/or structures (such as, for example, grooves or tabs) on the lower surface 20. Alternatively, reading location 10 may contain a removable slide. The assay device 12 can be loaded onto the slide prior to being inserted into the stand 2. The slide may also allow for assay devices 12 of different sizes/shapes to be inserted into the stand 2.

Figure 3:
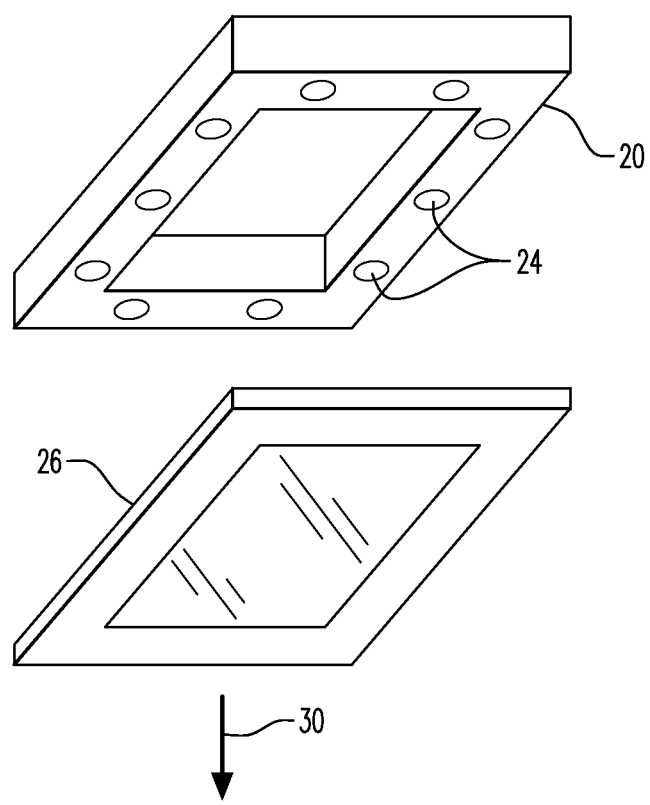
FIG. 3 illustrates a view of certain components of the stand of FIG. 1.

Assay device 12 may refer to a device whose aim is to measure an analyte in a liquid medium. Assay devices 12 may have a variety of shapes/configurations. For example, an assay device 12 may be an immunochromatography/immunocapture device (for example the Siemens CLINITEST hCG Pregnancy Test) or a common urine strip. FIGS. 1-3 depict the use of a urine strip but a person of ordinary skill in the art will understand that the various embodiments of this invention are not so limited. The urine strip assay devices 12 depicted in the Figs. typically contain a testing region 14 with a plurality of different testing pads arranged in a pre-established, known order. Each of the testing pads may contain a reagent. While each test pad in the Figs. is square, it should be understood that they may be any shape (for example circular, ovular, rectangular, etc.).

The distance 8 between the raised platform 6 and lower surface 20 may be selected to match, or approximate an optical focal length of the camera 18. As will be appreciated, the stand 2 can be optimized for an individual mobile computing device 4 or optimized such that it can accommodate a variety of different mobile computing devices 4. Accordingly, the distance 8 can be selected such that the stand 2 is compatible with a variety of mobile computing devices 4, for example, by selecting a distance 8 that is approximately equal to the focal length of the variety of mobile computing devices 4.

The stand 2 may also contain a light source 22 disposed between the reading location 10 and the raised platform 6. The light source 22 directs light 30 (denoted by arrow 30) away from the through hole 16 and towards the assay reading location area 10. As best shown in FIG. 3, which show the light source 22 from the bottom, the light source 22 is configured to allow the camera 18 an unobstructed view of the testing region 14 of the assay device 12 when the camera 18 of the mobile computing device 4 is aligned with the through hole 16 and when an assay device 12 is placed on the reading location 10. For example, the light source 22 can be arranged in a ring shape with individual lights 24 contained therein. The individual lights 24 may be arranged in light source 22 to illuminate the reading location 10 as evenly as possible. Alternatively, the stand 2 may allow light emanating from the mobile computing device 4, such as from the mobile computing device's 4 on board flash, to reach the testing region 14 instead of, or in addition to, the lighting source 22.

The stand 2 may also contain a first polarized lens 26 disposed between the light source 22 and the assay reading location 10, wherein substantially all of the light emanating from the individual lights 24 of the light source 22 pass through the first polarized lens 26. The first polarized lens may be polarized in a first direction. In one configuration, substantially all of the light 30 passes through the first polarized lens.

The stand 2 may further contain a second polarized lens 28 disposed between the camera 18 and the assay reading location 10. The second polarized lens 28 may be aligned with the through hole 16 such that when the camera 18 of the mobile computing device 4 is aligned with the through hole 16 and when an assay device 12 is placed on the reading location 10, the testing region 14 of the assay device 12 is visible to the camera 18 through the second polarized lens 28. The second polarized lens 28 may be polarized in a second direction that is substantially perpendicular to the first direction (the first and the second direction both being perpendicular the direction of light 30 (denoted by arrow 30). In one configuration, the second polarized lens 28 is positioned such that none, or almost none, of the light from light source 22 passes through the second polarized lens 28 prior to impacting the reading location 10. It should therefore be understood that light from the light source 22 must pass through the first polarized lens 26, bounce off of the assay device 12, and then pass through the second polarized lens 28 on its way to camera 18. This cross polarized light reduces problems associated with specular reflection off of a wet surface of the assay device 12.

In an embodiment of the invention, the stand 2 may contain one or more reference devices 36 located adjacent to the reading location 10 of the assay device 12. The reference device(s) 36 are present while the assay device 12 is being read by camera 18. In FIGS. 1 and 2, two reference devices 36 are located on either side of the assay device 12. Individual references devices 36 may contain a reference testing region 38 containing known reference color values (such as RGB values or values that can be converted to into RGB color). When an assay device 12 is disposed in the reading location 10, the reference testing region 38 of each the reference device 36 may be aligned with the testing region 14 of the assay device 12 such that both the reference testing region 38 and the testing region 14 are visible by the camera 18 through the second polarized lens 26. In an embodiment, such as that shown in FIGS. 1 and 2, reference device 36 have a reference testing region 38 which approximates the dimensions of the testing region 14 of assay device 12. Reference testing region 38 of reference device(s) may also be positioned in close proximity to the assay device 12 in order to ensure that the reference testing region 38 and the testing region 14 are similarly illuminated by light source 22.

In an illustrative method, processor 40 may either receive the known reference color values of the reference testing region 38 from an external source or retrieve the known reference color values from internal memory. The processor 40 and the camera 18 may then cooperate to obtain at least one measured color value of the testing region 14 of the assay device 12 and a corresponding measured color value of the reference testing region 38 of the reference device 36. The processor 40 may then receive/compare the known reference color values of the reference testing region 38 to the measured color value of the referencing testing region 14 to compute a correction value. Using the computed correction value, the processor may correct the measured color values of the testing region 14 of the assay device 12 to producing a corrected color value. The corrected color value may then be used to determine a result of the assay device 12. It should be appreciated that the presence of one or more reference devices 36 in stand 2 helps the processor 40 correct for small changes in illumination from light source 22 as well as the collection of dust in and/or the degradation of light source 22. Reference device(s) 36 also help correct for the penetration of exterior light into the stand 2.

In yet another embodiment, a reference device 36 may be placed in the reading location 10 with one or more additional reference devices 36 located on either side. Processor 40 in cooperation with the camera 18 may then view the reference device 36 in the reading location 10 and ascertain lighting variations along the length reference device 36. This information can then be used to determine a corrected color value of the testing region 14 of the assay device 12 once the assay device 12 is placed in the reading location 10.

In another illustrative method, processor 40 may be able to determine the order and location of each of testing pads on the assay device 12 by evaluating the received color information. Once located, the processor can focus on the RGB values which correspond to the center of each testing pad—which thereby improves the accuracy of the assay results. For example, the processor 40 may receive a plurality of RGB values obtained by camera 18 that correspond to the testing region of the assay device. The processor 40 may evaluate the received RGB values and identify a location of an "anchor testing pad" in the testing region matching a predefined RGB signature. The location of the anchor testing pad may then be used to determine the position of additional testing pads in the testing region of the assay device 12 based on the location of the anchor testing pad.

For example, the Siemens MultiStix 10SG strip has a blood reagent pad with a very high concentration of a background yellow dye. As shown in FIG. 7, this yellow dye affords a unique signature which is different than the other regent pads in the strip. This unique signature is seen in the middle of the figure below with the blue line approaching zero. The unique signature of the blood reagent pad allows this pad to be used as an "anchor pad 44" which becomes the starting point for determining the pad positions for the rest of the strip. The polystyrene backing also provides a unique signature which allows two things: 1) Can be used to give an idea of the light variation across the length of the strips, and 2) the Interval between the reagent pads on the strip. Using the found pad areas, the pixels within this found area are averaged to come up with mean Red, Green, and Blue signals. These signals can be converted into a form which allows a dose response to the analyte to be constructed.

FIGS. 4A-5B depict an illustrative method of correcting for non-uniform lighting. FIG. 6 represents an illustrative photograph, taken by camera 18, of reading location 10. In this example, a reference device 36 is located in reading location 10 (instead of an assay device 12) and a reference device 36 is located on either side of the reading location 10. The three reference devices 36 may be the same color(s)— for example gray. Three positions (positions 42A, 42B, and 42C) on each of the three gray strips are then analyzed to obtain RGB values. Calibration is then performed side-to-side as well as front-to-back to adjust for lighting variations along the length of the devices.

Figure 4A:
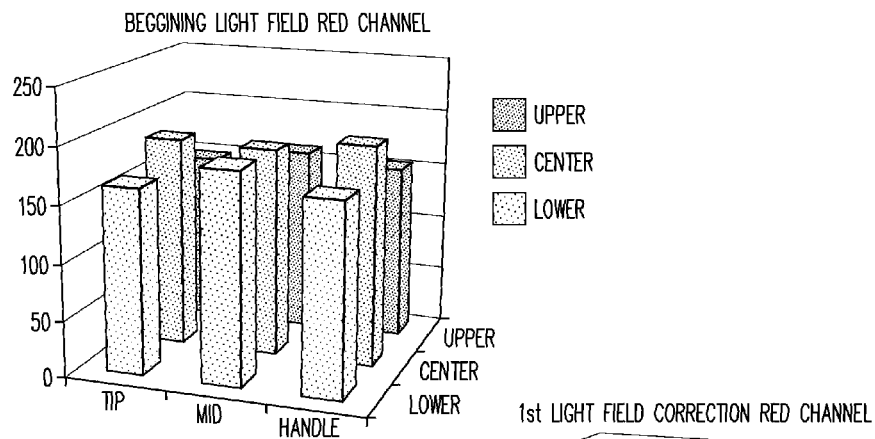

The obtained beginning light field red channel values are represented in FIG. 4A. Note that the lighting at three positions in the center strip varies along it and varies relative to the parallel reference strips. In this case, the lighting is weaker on the ends of the (positions 42A and 42C) reference testing regions 38 of the reference devices 36 but is weaker in the middle for reference testing regions 38 (position 42B). Overall, the center of the reference testing regions 38 has stronger lighting than the reference strips.

Figure 4B:
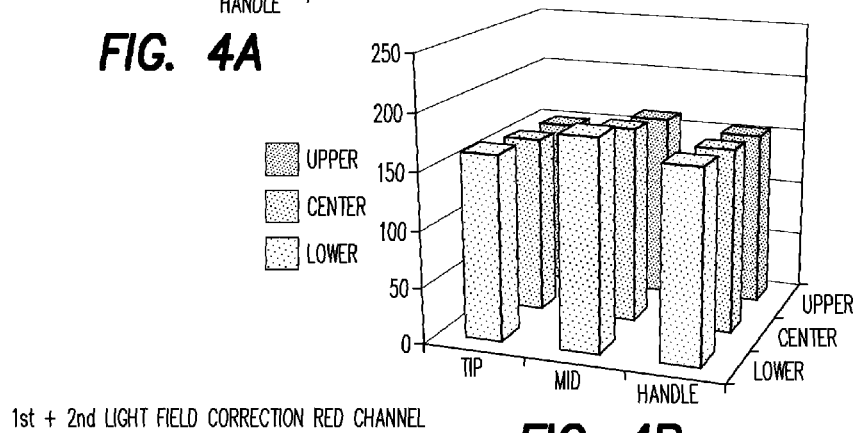
Figure 4C:
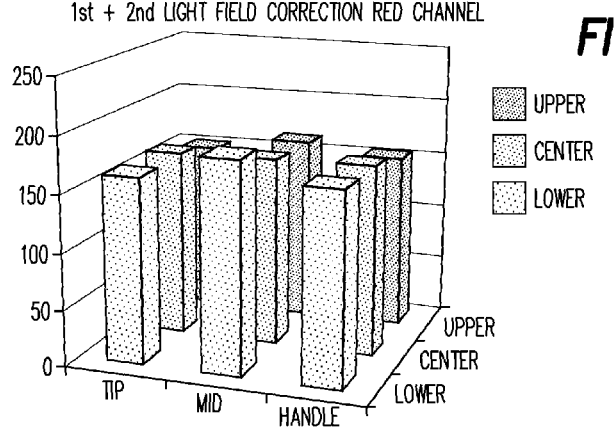

FIG. 4B represents a first correction which considers the center reference device relative to the standards at the first position 42A, without regard to the second position 42B or the third position 42C; then at the second position 42B without regard to the first or third positions 42A and 42C; and then at the third position 42C without regards to the first or the second positions 42A and 42B. FIG. 4C represents a second correction which equalizes along the strip length.

The same operations are done for the Green (G) channel data and the Blue (B) Channel Data.

Figure 5A:
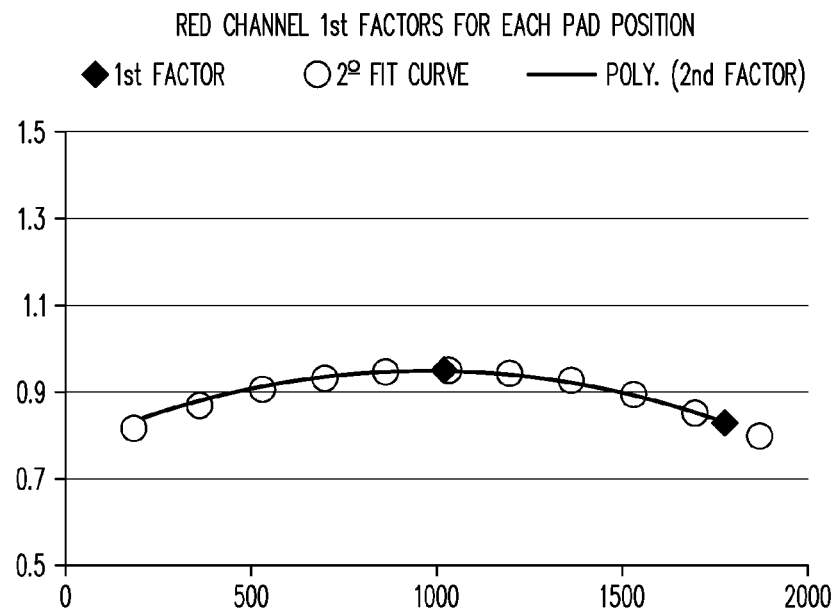
Figure 5B:
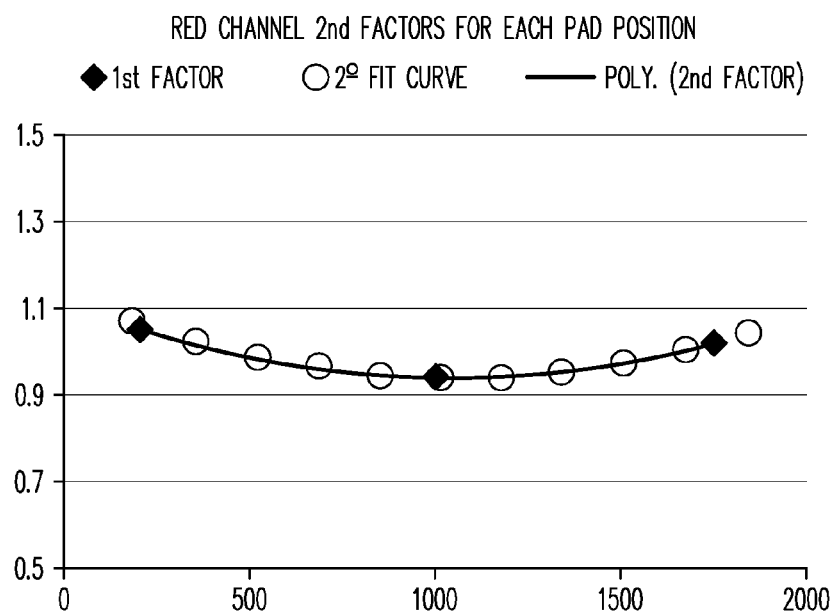

The results of the above corrections are then plotted—as represented in FIGS. 5A and 5B. The green circles in the plots represent correction factors for the pad center positions. Notice that there are both "Under range" and "Over range" calculations using the polynomial curve slightly beyond the input data points (calibration points). This is OK if the calculation is made just slightly outside of the calibrator range.

Where, for example, the individual lights 24 are White LED's (which are a combination of Blue stimulator and Yellow Fluor) a close relationship of Red and Green channel correction factors may be expected, but the Blue channel may throw a somewhat different pattern on the observation area.

For the second order polynomial type correction shown, the light field may be optically uniform to the extent that differences are only discernable among thirds of the reference testing region 38 of reference device 36 and the testing region 14 of the assay devices 12, respectively. This may be done by adding a translucent or holographic scattering filter in front of the light source 22. If the light has a smaller scale structure, such as light variation from 1 cm to the next, then this second degree polynomial type correction would help or it may be applied in smaller sections of the observation field. Similarly, if the light field were controlled so that variations only appeared significantly for distances similar to the length of testing regions, then a first degree (slope and intercept) type correction may suffice. And if the light field were of particularly good uniformity, then a single point correction may provide overall light level.

FIG. 8 depicts an illustrative user interface 46 for an Android device. The interface 46 can provide instructions for the proper technique and use of the assay device 12 and the stand 3. Results may then displayed and additional medical information can be provided for any of the analytes tested in the assay device 12.

It should be understood that any of the above methods and/or actions performed by the mobile computing device 4 are implemented by the processor 40. Processor 40 is coupled to a non-transitory computer-readable storage medium 41 in which computer-executable instructions are stored. These stored instructions, when executed by the processor 40, instruct processor 40 to form the actions described above. Stated differently, it is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

What is claimed is:
1. A stand for a mobile computing device, the stand comprising:

a reading location capable of supporting an assay device having a testing region;

at least one reference device located adjacent to the reading location on a first side of the assay device when the assay device is supported by the reading location, the reference device containing a reference testing region, the reference testing region having known reference color values, the reference testing region being aligned with the testing region of the assay device when the assay device is being supported by the reading location;

a raised platform disposed a distance above the reading location along a first line extending from the raised platform to the reading location, the raised platform having a through hole, the through hole capable of being aligned with a camera on the mobile computing device when the mobile computing device is placed on the raised platform, the through hole allowing the camera an unobstructed view of the testing region of the assay device and the reference testing region of the reference device;

a light source disposed between the reading location and the raised platform, the light source directing light at the reading location and the reference testing region substantially along the first line, the light source not obstructing the camera's unobstructed view of the testing region of the assay device when the camera of the mobile computing device is aligned with the through hole and when the assay device is placed on the reading location; and at least one exterior surface, wherein the combination of the raised platform and the at least one exterior surface prevent substantially all external light from reaching the reading location, wherein external light is lighting emanating from outside of the stand, wherein the mobile computing device further comprises a processor operatively coupled to the camera.

2. The stand of claim 1 wherein the at least one reference device is a first reference device and, further comprising:

a second reference device located adjacent to the reading location on the first side of the assay device when the assay device is supported by the reading location, the second reference device containing a reference testing region, the reference testing region of the second reference device having known reference color values, the reference testing region of the second reference device being aligned with the testing region of the assay device when the assay device is being supported by the reading location.

3. A non-transitory computer-readable storage medium on which computer-executable instructions are stored, the computer-executable instructions, when executed by a computing device, implementing a method of using the stand of claim 1, the method implemented by the computer-executable instructions comprising:

receiving the known reference color values of the reference testing region;

obtaining at least one measured color value of the testing region of the assay device and a corresponding measured color value of the reference testing region of the reference device;

receiving and comparing the known reference color values of the reference testing region to the measured color value of the testing region;

using the known reference color values to correct the measured color values and producing a corrected color value; and using the corrected color value to determine a result of the assay.

4. The stand of claim 1, wherein the light source is positioned to front light the reading location and the reference testing region.

5. The stand of claim 1, wherein the through hole in the raised platform is sized to block a flash on the mobile computing device.

6. A stand for a mobile computing device, the stand comprising:

a reading location capable of supporting an assay device having a testing region;

at least one reference device located adjacent to the reading location on a first side of the assay device when the assay device is supported by the reading location, the reference device containing a reference testing region, the reference testing region having known reference color values, the reference testing region being aligned with the testing region of the assay device when the assay device is being supported by the reading location;

a raised platform disposed a distance above the reading location along a first line extending from the raised platform to the reading location, the raised platform having a through hole, the through hole capable of being aligned with a camera on the mobile computing device when the mobile computing device is placed on the raised platform, the through hole allowing the camera an unobstructed view of the testing region of the assay device and the reference testing region of the reference device;

a light source disposed between the reading location and the raised platform, the light source directing light at the reading location and the reference testing region substantially along the first line, the light source not obstructing the camera's unobstructed view of the testing region of the assay device when the camera of the mobile computing device is aligned with the through hole and when the assay device is placed on the reading location;

a first polarized lens disposed between the light source and the reading location, the first polarized lens polarized in a first direction;

a second polarized lens disposed between the raised platform and the reading location, the second polarized lens polarized in a second direction such that light emitted by the light source passes through the first polarized lens and the second polarized lens to cross polarize light reaching the through hole in the raised platform; and at least one exterior surface, wherein the combination of the raised platform and the at least one exterior surface prevent substantially all external light from reaching the reading location, wherein external light is lighting emanating from outside of the stand, wherein the mobile computing device further comprises a processor operatively coupled to the camera.

7. The stand of claim 6, wherein the at least one reference device is a first reference device and, further comprising:

a second reference device located adjacent to the reading location on the first side of the assay device when the assay device is supported by the reading location, the second reference device containing a reference testing region, the reference testing region of the second reference device having known reference color values, the reference testing region of the second reference device being aligned with the testing region of the assay device when the assay device is being supported by the reading location.

8. The stand of claim 6, wherein the light source is positioned to front light the reading location and the reference testing region.

9. The stand of claim 6, wherein the through hole in the raised platform is sized to block a flash on the mobile computing device.

10. The stand of claim 6, wherein the second polarized lens is aligned with the through hole.

11. The stand of claim 6, wherein the second direction is substantially perpendicular to the first direction.

12. The stand of claim 6, wherein the second polarized lens is positioned such that none of the light from the light source passes through the second polarized lens prior to impacting the reading location.

13. The stand of claim 6, wherein the first polarized lens is positioned such that substantially all of the light from the light source passes through the first polarized lens.

* * * * *